United States Patent [19]
Tixidre et al.

[11] Patent Number: 5,716,841
[45] Date of Patent: Feb. 10, 1998

[54] PROCESS FOR THE RESOLUTION OF ETHYL 4,4,4-TRIFLUORO-3(R)-HYDROXYBUTANOATE USING LIPASE FROM CANDIDA

[75] Inventors: Arlette Tixidre, Orsay; Lydia Zard, Gif sur Yvette; Guy Rossey, Voisins Le Bretonneux; André Bourbon, La Chaussée d'Ivry, all of France

[73] Assignee: Synthelabo, Le Plessis Robinson, France

[21] Appl. No.: 628,166

[22] Filed: Apr. 5, 1996

[30] Foreign Application Priority Data

Apr. 7, 1995 [FR] France ................... 95 04141

[51] Int. Cl.$^6$ ................................. C12P 41/00
[52] U.S. Cl. ................................. 435/280
[58] Field of Search ........................ 435/280

[56] References Cited

FOREIGN PATENT DOCUMENTS

| 334966 | 10/1989 | European Pat. Off. |
| 0 424 244 | 4/1991 | European Pat. Off. |
| 89 02916 | 4/1989 | WIPO . |

OTHER PUBLICATIONS

Lin et al., "A Microbially Based Approach for the preparation of Chiral Molecules Possessing the Trifluoromethyl Group", J. Org. Chem., vol. 52, No. 15 (1987) pp. 3211–3217.

Chemical Abstracts, vol. 116, No. 12, (1992), Abstract No. 127023d, p. 718, JP–A–03 254 694 (Kurita Water Ind.) 13 Nov. 1991.

Chemical Abstracts, vol. 113, No. 7, (1990) Abstract No. 57476r, p. 560, JP–A–02 040 343 (Meito Sangyo) Feb. 1990.

Chemical Abstracts, vol. 120, No. 3, (1994) Abstract No. 29497, Myazawa, Toshifumi et al. Microbial Manufacture of Optically Actiive Halogen–Containing Alcohols', JP–A–05 219 986.

Chem. Abstr., vol. 110, No. 13, (1989) Abstract No. 113136g, Kitazume, "A Microbially Based Approach for the Preparation of Fluorinated Ferroelectric Liquid Crystals".

Ehrler et al., "Noitz Uber Mikrobiologisch Umsetzungen Mit Halobacterium...." Helvetica Chimica Acta., vol. 72, No. 4, (1989) pp. 793–799.

*Primary Examiner*—Sandra E. Saucier
*Attorney, Agent, or Firm*—Foley & Lardner

[57] ABSTRACT

A process for the preparation of ethyl 4,4,4-trifluoro-3(R)-hydroxybutanoate, wherein the ester functional group of the (S) enantiomer of ethyl (±)-4,4,4-trifluoro-3-hydroxybutanoate which comprises (R) and (S) is selectively hydrolysed in aqueous medium, by means of a lipase, and the non-hydrolysed (R) enantiomer is then extracted and used in the preparation of 4,4,4-trifluoro-1,3(R)-butanediol.

16 Claims, No Drawings

PROCESS FOR THE RESOLUTION OF ETHYL 4,4,4-TRIFLUORO-3(R)-HYDROXYBUTANOATE USING LIPASE FROM CANDIDA

The present invention relates to a new process for the preparation of ethyl 4,4,4-trifluoro-3(R)-hydroxybutanoate and its use in the preparation of 4,4,4-trifluoro-1,3(R)-butanediol, an intermediate in the synthesis of 3-[4-(4,4,4-trifluoro-3(R)-hydroxybutoxy)phenyl]-5 (R)-methoxymethyl-2-oxazolidinone (befloxatone).

Befloxatone is a compound which is useful as an inhibitor of monoamine oxidase A, and is described in European Patent Application EP-A-0424244.

According to the process described in EP-A-0424244, befloxatone is obtained by reaction of 3-(4-hydroxyphenyl)-5(R)-methoxymethyl-2-oxazolidinone with 4,4,4-trifluoro-1-tosyloxy-3(R)-butanol, the latter compound being itself prepared from ethyl (±)-4,4,4-trifluoro-3-hydroxybutanoate via the intermediacy of (±)-4,4,4-trifluoro-3-hydroxybutanoic acid, 4,4,4-trifluoro-3(R)-hydroxybutanoic acid and 4,4,4-trifluoro-1,3(R)-butanediol.

According to this process, ethyl (±)-4,4,4-trifluoro-3-hydroxybutanoate is converted to the sodium salt of the corresponding butanoic acid which is hydrolysed to give (±)-4,4,4-trifluoro-3-hydroxbutanoic acid, this acid is reacted with (S)-α-methylbenzylamine, the (S)-α-methylbenzylamine salt of 4,4,4-trifluoro-3(R)-hydroxybutanoic acid is separated from the mixture of diastereoisomers formed by crystallization from ethanol and this salt is then hydrolysed in acid medium to produce 4,4,4-trifluoro-3(R)-hydroxybutanoic acid. 4,4,4-Trifluoro-1,3(R)-butanediol is then obtained by reduction of 4,4,4-trifluoro-3(R)-hydroxybutanoic acid.

The present invention relates to the preparation of ethyl 4,4,4-trifluoro-3(R)-hydroxybutanoate which is the precursor of 4,4,4-trifluoro-1,3(R)-butanediol which is used as intermediate in the synthesis of befloxatone.

According to the present invention there is provided a process for the preparation of ethyl 4,4,4-trifluoro-3(R)-hydroxybutanoate, wherein the ester functional group of the (S) enantiomer of ethyl (±)-4,4,4-trifluoro-3-hydroxybutanoate which comprises (R) and (S) enantiomers is selectively hydrolysed in aqueous medium, by means of a lipase, and the non-hydrolysed (R) enantiomer is then extracted.

According to the invention, ethyl 4,4,4-trifluoro-3(R)-hydroxybutanoate is obtained by selective enzymatic hydrolysis of the ester functional group of ethyl (±)-4,4,4-trifluoro-3-hydroxybutanoate by means of a lipase, which results in a mixture of 4,4,4-trifluoro-3(S)-hydroxybutanoic acid and of ethyl 4,4,4-trifluoro-3(R)-hydroxybutanoate, and extraction of the non-hydrolysed (R) enantiomer.

The process of the invention is represented in Scheme 1:

Scheme 1

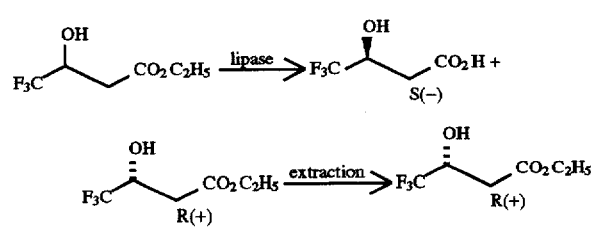

The lipase used is, for example, *Candida cylindracea* lipase (lipase-MY, Meito Sangyo Co. Ltd., Japan), Candida lipase (lipase-AY, Amano, Japan) or, preferably, *Candida antarctica* lipase, preferably immobilized on a resin (eg. Novozym® 435, Novo Nordisk, Denmark).

The aqueous medium is, for example, a phosphate buffer solution or an aqueous potassium bicarbonate solution, and the hydrolysis is carried out at, typically, a temperature of from 20° to 40° C., for from 1 to 18 hours.

Generally, Novozym® 435 is used at a concentration of from 0.1 to 10% and the lipases AY and MY at concentrations of from 5 to 20% with respect to the weight of substrate.

The non-hydrolysed (R) enantiomer is recovered generally by extraction in an organic solvent whereas the (S) enantiomer, which is hydrolysed to the acid, remains in the aqueous phase at basic pH.

4,4,4-Trifluoro-1,3(R)-butanediol is then obtained in a single stage by reduction of ethyl 4,4,4-trifluoro-3 (R)-hydroxybutanoate.

Examples 1 and 2 illustrate the invention.

Example 1

Ethyl 4,4,4-trifluoro-3(R)-hydroxybutanoate 3 mg of Novozym® 435 are added to 2 g of ethyl (±)-4,4,4-trifluoro-3-hydroxybutanoate in suspension in 50 ml of 0.01 M phosphate buffer ($KH_2PO_4+Na_2HPO_4$), pH=7.2, and the reaction mixture is then stirred for 17 h at 22° C., the pH being kept constant by addition of a 1 M aqueous sodium hydroxide solution.

The extraction is then carried out at pH=9 with dichloromethane and the organic phases are then combined, subsequently dried over magnesium sulphate, filtered and evaporated under vacuum.

0.74 g of product is thus obtained (Yield=74%).

$[\alpha]_D^{20}$=+15° (chloroform, C=0.914) ee:>98% (chiralcel OD-R HPLC).

EXAMPLE 2

Ethyl 4,4,4-trifluoro-3(R)-hydroxybutanoate 600 g of ethyl (±)-4,4,4-trifluoro-3-hydroxybutanoate, 6 liters of demineralized water, 323 g of potassium bicarbonate and 30 g of Novozym® 435 are introduced into a 10 liter reactor. The mixture is stirred for 1 h 10 min, the enzyme is then filtered off on sintered glass and 1 kg of sodium chloride is added to the filtrate. The mixture is stirred until dissolved and the mixture is then extracted with 2 times 2 liters and then 2 times 1 liter of dichloromethane. The combined organic phases are washed with 1 liter of water saturated with sodium chloride and the solvent is then evaporated at atmospheric pressure. 205.4 g of product containing 12% of dichloromethane are obtained (Corrected yield: 60.2%).

$[\alpha]_D^{20}$=+14.59° (chloroform, c=1) ee=96.7% (Chiralpack AD HPLC)

Ethyl 4,4,4-trifluoro-3(R)-hydroxybenzoate can then be converted to 4,4,4-trifluoro-1,3(R)-butanediol in a single stage.

Example 3 illustrates the use of ethyl 4,4,4-trifluoro-3(R)-hydroxybenzoate in the preparation of 4,4,4-trifluoro-1,3 (R)-butanediol.

EXAMPLE 3

4,4,4-Trifluoro-1,3(R)-butanediol

A solution of 100 g of ethyl 4,4,4-trifluoro-3(R)-hydroxybutanoate in 80 ml of absolute ethanol is poured dropwise, under argon, while not exceeding 35° C., on to a suspension of 20.4 g of sodium borohydride in 270 ml of absolute ethanol. The reaction mixture is then stirred for 16 h, is then poured into ice-cold water and 150 ml of a concentrated aqueous hydrochloric acid solution are added. Extraction is then carried out with 3 times 250 ml of ethyl acetate and the organic phase is dried over sodium sulphate, filtered and evaporated under vacuum. 64.6 g of a hazy liquid are obtained, which liquid is purified by distillation under vacuum. 53 g of product are finally obtained.

Yield: 69%. Boiling point: 68–75° C. (under 66 Pa, i.e. 0.5 mm Hg). $[\alpha]_D^{20} = +26.1°$ (c=0.548, chloroform).

This new method, which makes it possible to obtain 4,4,4-trifluoro-1,3(R)-butanediol in only three stages, including a simple extraction, from ethyl (±)-4,4,4-trifluoro-3-hydroxybutanoate and with a high yield, which improves the overall synthesis of befloxatone.

We claim:

1. A process for the preparation of ethyl 4,4,4-trifluoro-3(R)-hydroxybutanoate comprising the steps of:
   (a) selectively hydrolyzing in aqueous medium the ester functional group of the (S) enantiomer of ethyl (R,S)-4,4,4-trifluoro-3-hydroxybutanoate, said (S) enantiomer being in a mixture comprising (R) and (S) enantiomers of ethyl 4,4,4-trifluoro-3-hydroxybutanoate, by means of a Candida lipase; and
   (b) extracting the non-hydrolyzed (R) enantiomer.

2. The process of claim 1, wherein the lipase is immobilized on a resin.

3. The process of claim 1, wherein the lipase is used at concentration of from 0.1% to 10% by weight, based on the weight of the substrate.

4. The process of claim 1, wherein the lipase is used at a concentration of from 5% to 20% by weight, based on the weight of the substrate.

5. The process of claim 1, wherein the lipase is a *Candida antarctica* lipase.

6. The process of claim 5, wherein the lipase is immobilized on a resin.

7. The process of claim 5, wherein the lipase is used at a concentration of from 0.1% to 10% by weight, based on the weight of the substrate.

8. The process of claim 1, wherein the lipase is a *Candida cylindracea* lipase.

9. The process of claim 8, wherein the lipase is a Lipase-MY.

10. The process of claim 9, wherein the lipase is used at a concentration of 5% to 20% by weight, based on the weight of the substrate.

11. The process of claim 1, wherein the lipase is a Lipase-AY.

12. The process of claim 11, wherein the lipase is used at a concentration of 5% to 20% by weight, based on the weight of the substrate.

13. The process of claim 1, wherein said aqueous medium is selected from the group consisting of a phosphate buffer solution and a potassium bicarbonate solution.

14. The process of claim 1, wherein said hydrolysis is carried at a temperature of from 20° C. to 40° C.

15. In a process for making 3-[4-(4,4,4-trifluoro-3(R)-hydroxybutoxy)phenyl]-5(R)-methoxy methyl-2-oxazolidinone from 4,4,4-trifluoro-1,3(R)-butanediol, wherein the improvement comprises making the 4,4,4-trifluoro-1,3(R)-butanediol by reducing ethyl 4,4,4-trifluoro-3(R)-hydroxybutanoate which is made by the process of any one of claims 1–14.

16. In a process for making 4,4,4-trifluoro-1,3(R)-butanediol by reducing ethyl 4,4,4-trifluoro-3(R)-hydroxybutanoate, wherein the improvement comprises making said ethyl 4,4,4-trifluoro-3(R)-hydroxybutanoate by the process of any one of claims 1–14.

\* \* \* \* \*